US012784870B2

(12) United States Patent
Dutta et al.

(10) Patent No.: US 12,784,870 B2
(45) Date of Patent: Nov. 3, 2026

(54) METHOD AND SYSTEM FOR DETERMINING FREE ENERGY OF PERMEATION FOR MOLECULES

(71) Applicant: Tata Consultancy Services Limited, Mumbai (IN)

(72) Inventors: Prantar Dutta, Pune (IN); Rakesh Gupta, Pune (IN); Deepak Shyamsunder Jain, Pune (IN); Beena Rai, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 947 days.

(21) Appl. No.: 18/163,215

(22) Filed: Feb. 1, 2023

(65) Prior Publication Data

US 2023/0307087 A1 Sep. 28, 2023

(30) Foreign Application Priority Data

Mar. 23, 2022 (IN) ............................. 202221016248

(51) Int. Cl.
*G16B 5/30* (2019.01)
*G16B 40/00* (2019.01)

(52) U.S. Cl.
CPC ............... *G16B 5/30* (2019.02); *G16B 40/00* (2019.02)

(58) Field of Classification Search
CPC ........ G16B 5/30; G16B 40/00; G06N 3/0442; G06N 3/045; G06N 3/084; G16C 10/00; G16C 20/70; G16C 20/30
See application file for complete search history.

(56) References Cited

U.S. PATENT DOCUMENTS

2008/0147360 A1* 6/2008 Fejes ....................... G06F 30/20 703/2

OTHER PUBLICATIONS

Yonezawa, Yasushige. "Effective computational method for evaluation of dynamic elecrostatic effects of explicit solvent and membrane molecules from molecular dynamics simulations." 2011 IEEE Seventh International Conference on e-Science Workshops. IEEE, 2011 (Year: 2011).*

(Continued)

*Primary Examiner* — Saif A Alhija
(74) *Attorney, Agent, or Firm* — Finnegan, Henderson, Farabow, Garrett & Dunner, LLP

(57) ABSTRACT

State of the art systems being used for determining free energy of permeation have the disadvantages that estimations purely based on molecular simulations is computationally expensive, and thus not suitable for high throughput calculation and screening. Existing machine learning approaches suffer from low accuracy and generalizability. The free energy of permeation is based on the molecule only, without considering lipid membranes. Hence, the models can't capture the difference between lipids. The disclosure herein generally relates to molecular processing, and, more particularly, to a method and system for determining free energy of permeation for molecules. The system creates features based on interaction of a molecule with solvent and lipid membranes. The features are then processed to determine time dependency, feature dependency, and feature relevance, and in turn the free energy of permeation is determined. The determined free energy of permeation is then given as a recommendation to a user.

12 Claims, 10 Drawing Sheets

200

(56) References Cited

OTHER PUBLICATIONS

Batra, Rohit, and Subramanian Sankaranarayanan. "Machine learning for multi-fidelity scale bridging and dynamical simulations of materials." Journal of Physics: Materials 3.3 (2020): 031002. (Year: 2020).*

Zeng, Wenqi et al., "A Note on Learning Rare Events in Molecular Dynamics using LSTM and Transformer", Computational Physics, Date: Jul. 2021, Publisher: Arxiv, https://arxiv.org/pdf/2107.06573.pdf.

Pandey, Poonam, "Prediction of Membrane Permeation of Small Drug Molecules using Silcs Energy Profile with Machine Learning", Biophysical Journal, Date: Feb. 2021, Publisher: Research Gate, https://www.researchgate.net/publication/349272073_Prediction_of_Membrane_Permeation_of_Small_Drug_Molecules_using_Silcs_Energy_Profile_with_Machine_Learning/link/60a5455245851605a0b24459/download.

Martinotti, Carlo et al., "Molecular dynamics simulation of the interaction of small molecules with biological membranes", ChemPhysChem, Date: May 2020, Publisher: ACS Publications, https://www.researchgate.net/publication/341642441_Molecular_dynamics_simulation_of_the_interaction_of_small_molecules_with_biological_membranes/link/5edde4ae299bf1c67d506ff6/download.

* cited by examiner

METHOD AND SYSTEM FOR DETERMINING FREE ENERGY OF PERMEATION FOR MOLECULES

PRIORITY CLAIM

This U.S. patent application claims priority under 35 U.S.C. § 119 to: Indian Patent Application No. 202221016248, filed on Mar. 23, 2022. The entire contents of the aforementioned application are incorporated herein by reference.

TECHNICAL FIELD

The disclosure herein generally relates to molecular processing, and, more particularly, to a method and system for determining free energy of permeation of molecules across the lipid membranes

BACKGROUND

The biological barriers such as human skin, intestine, cells, and blood brain barrier are surrounded by the lipid membranes. Permeability is an important characteristic of molecules, which determines/represents capability of the molecules to pass through these barriers. The permeability of molecules across these lipid membranes depends upon their diffusion and free energy of permeation across the lipid membranes. For example, a molecule (drug, nutritious compound) taken orally, passes through the stomach and reaches to the intestinal lipid membrane and the permeation of this active through this membrane determines its final concentrations in the systematic circulation. In another example, molecules (cosmetic ingredients) applied on the skin having a significant permeability could be used to serve intended purposes. The permeability of the molecules could be obtained using the experimental procedures using the cell lines and artificial tissues, however these methods are expensive, and requires experts and dedicated experimental facilities.

The free energy of permeation can also be determined using computational techniques such as molecular dynamics simulations and more recently using machine learning and artificial intelligence methods. State of the art techniques that are being used for determining free energy of permeation of molecules have been identified to have the following disadvantages. Estimating free energy of permeation purely based on molecular simulations is computationally expensive, and thus not suitable for high throughput calculation and screening. Machine Learning approaches suffer from low accuracy and generalizability. The free energy of permeation calculated utilizing the machine learning method only accounts for features obtained from molecules, without considering lipid membranes. Hence, the models can't capture the difference between lipids present in various biological barriers (skin, intestine, blood brain barrier and cell membranes).

SUMMARY

Embodiments of the present disclosure present technological improvements as solutions to one or more of the above-mentioned technical problems recognized by the inventors in conventional systems. For example, in one embodiment, a processor implemented method is provided. In this method, initially a first set of features is generated via one or more hardware processors, based on interaction of a molecule with a lipid membrane, by performing a molecular dynamics simulation, wherein values of the first set of features are collected as a time series data. Further, a second set of features is generated via the one or more hardware processors, based on interaction of the molecule with a solvent, by performing the plurality of molecular dynamics simulations, wherein values of the second set of features are collected as a time series data. Further, a concatenated data set comprising values of the first set of features and the second set of features is generated, via the one or more hardware processors, wherein the values of the first set of features and the second set of features are extracted from a plurality of instances of the time series data of the first set of features and the second set of features. Further, the concatenated data set is pre-processed via the one or more hardware processors to generate a pre-processed data set. Further, the pre-processed data set is represented in a 2-Dimensional (2D) array format via one or more hardware processors. Further, a free energy of permeation is generated via the one or more hardware processors, by processing the pre-processed data set in the 2D array format using a machine learning data model. Processing the pre-processed data set in the 2D array format using the machine learning data model includes the following steps. A context vector comprising information on time dependency, feature relevance, and similarity, for a plurality of molecule-lipid membrane combinations in the pre-processed data set stored in the 2D array format, is generated. Further, a transformed vector comprising information on non-linear dependency of the components of the context vector, is generated. Further, the free energy of permeation is generated as weighted sum of components of the transformed vector.

In another aspect, a system is provided. The system includes one or more hardware processors, a communication interface, and a memory (104) storing a plurality of instructions, wherein the plurality of instructions when executed, cause the one or more hardware processors to initially generate a first set of features, based on interaction of a molecule with a lipid membrane, by performing a plurality of molecular dynamics simulations, wherein values of the first set of features are collected as a time series data. Further, the system generates a second set of features via the one or more hardware processors, based on interaction of the molecule with a solvent, by performing the plurality of molecular dynamics simulations, wherein values of the second set of features are collected as a time series data. Further, a concatenated data set comprising values of the first set of features and the second set of features is generated, via the one or more hardware processors, wherein the values of the first set of features and the second set of features are extracted from a plurality of instances of the time series data of the first set of features and the second set of features. Further, the concatenated data set is pre-processed via the one or more hardware processors to generate a pre-processed data set. Further, the pre-processed data set is represented in a 2-Dimensional (2D) array format via one or more hardware processors. Further, a free energy of permeation is generated via the one or more hardware processors, by processing the pre-processed data set in the 2D array format using a machine learning data model. Processing the pre-processed data set in the 2D array format using the machine learning data model includes the following steps. A context vector comprising information on time dependency, feature relevance, and similarity, for a plurality of molecule-lipid membrane combinations in the pre-processed data set stored in the 2D array format, is generated. Further, a transformed vector comprising information on non-linear dependency of the components of the context vector, is generated. Further, the free energy of permeation is generated as weighted sum of components of the transformed vector.

In yet another aspect, a non-transitory computer readable medium is provided. A plurality of instructions in the non-transitory computer readable medium when executed, cause one or more hardware processors to perform the following steps. Initially, a first set of features is generated via the one or more hardware processors, based on interaction of a molecule with a lipid membrane, by performing a plurality of molecular dynamics simulations, wherein values of the first set of features are collected as a time series data. Further, a second set of features is generated via the one or more hardware processors, based on interaction of the molecule with a solvent, by performing the plurality of molecular dynamics simulations, wherein values of the second set of features are collected as a time series data. Further, a concatenated data set comprising values of the first set of features and the second set of features is generated, via the one or more hardware processors, wherein the values of the first set of features and the second set of features are extracted from a plurality of instances of the time series data of the first set of features and the second set of features. Further, the concatenated data set is pre-processed via the one or more hardware processors to generate a pre-processed data set. Further, the pre-processed data set is represented in a 2-Dimensional (2D) array format via one or more hardware processors. Further, a free energy of permeation is generated via the one or more hardware processors, by processing the pre-processed data set in the 2D array format using a machine learning data model. Processing the pre-processed data set in the 2D array format using the machine learning data model includes the following steps. A context vector comprising information on time dependency, feature relevance, and similarity, for a plurality of molecule-lipid membrane combinations in the pre-processed data set stored in the 2D array format, is generated. Further, a transformed vector comprising information on non-linear dependency of the components of the context vector, is generated. Further, the free energy of permeation is generated as weighted sum of components of the transformed vector.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
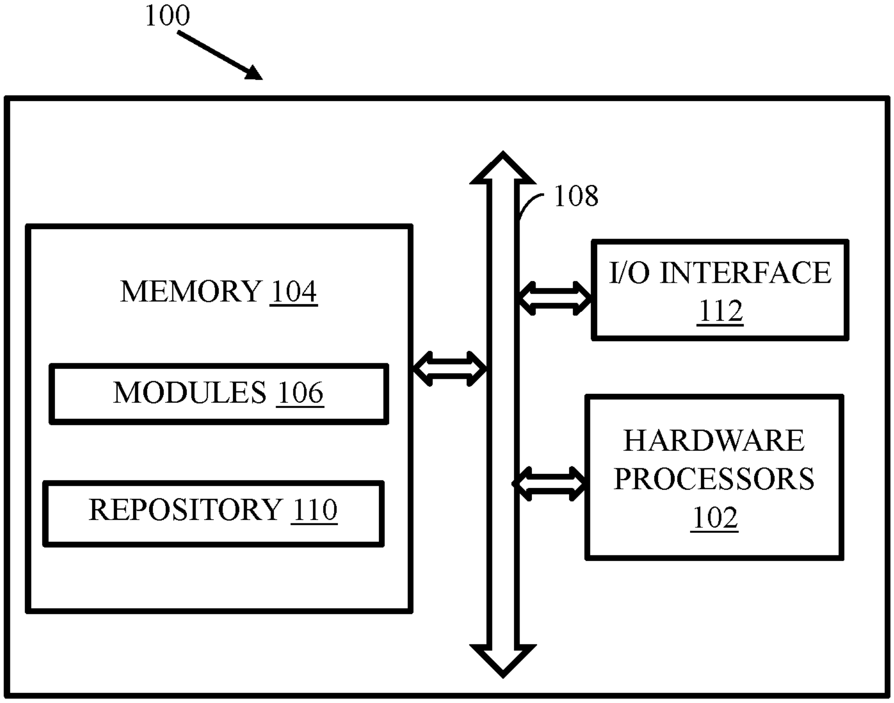
FIG. 1 illustrates an exemplary system for determining free energy of permeation, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Permeability is an important characteristic of molecules, which determines/represents capability of the molecules to pass through various membranes. For example, molecules of a drug, when ingested to a human body, may have to pass through various membranes in the body to reach a target cell. In another example, various molecules in cosmetic products also are required to have specific permeability values to serve intended purposes. Traditional systems estimating free energy of permeation purely based on molecular simulations are computationally expensive, and thus not suitable for high throughput calculation and screening. Existing machine learning approaches suffer from low accuracy and generalizability. The free energy of permeation is based on the molecule only, without considering lipid membranes. Hence, the models can't capture the difference between lipids.

Referring now to the drawings, and more particularly to FIG. 1 through FIG. 8C, where similar reference characters denote corresponding features consistently throughout the figures, there are shown preferred embodiments and these embodiments are described in the context of the following exemplary system and/or method.

FIG. 1 illustrates an exemplary system for determining free energy of permeation, according to some embodiments of the present disclosure. The system 100 includes or is otherwise in communication with hardware processors 102, at least one memory such as a memory 104, an I/O interface 112. The hardware processors 102, memory 104, and the Input/Output (I/O) interface 112 may be coupled by a system bus such as a system bus 108 or a similar mechanism. In an embodiment, the hardware processors 102 can be one or more hardware processors.

The I/O interface 112 may include a variety of software and hardware interfaces, for example, a web interface, a graphical user interface, and the like. The I/O interface 112 may include a variety of software and hardware interfaces, for example, interfaces for peripheral device(s), such as a keyboard, a mouse, an external memory, a printer and the like. Further, the I/O interface 112 may enable the system 100 to communicate with other devices, such as web servers, and external databases.

The I/O interface 112 can facilitate multiple communications within a wide variety of networks and protocol types, including wired networks, for example, local area network (LAN), cable, etc., and wireless networks, such as Wireless LAN (WLAN), cellular, or satellite. For the purpose, the I/O interface 112 may include one or more ports for connecting several computing systems with one another or to another server computer. The I/O interface 112 may include one or more ports for connecting several devices to one another or to another server.

The one or more hardware processors 102 may be implemented as one or more microprocessors, microcomputers, microcontrollers, digital signal processors, central processing units, node machines, logic circuitries, and/or any devices that manipulate signals based on operational instructions. Among other capabilities, the one or more hardware processors 102 is configured to fetch and execute computer-readable instructions stored in the memory 104.

The memory 104 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes. In an embodiment, the memory 104 includes a plurality of modules 106.

The plurality of modules 106 include programs or coded instructions that supplement applications or functions performed by the system 100 for executing different steps involved in the process of determining the free energy of permeability of molecules, being performed by the system 100. The plurality of modules 106, amongst other things, can include routines, programs, objects, components, and data structures, which performs particular tasks or implement particular abstract data types. The plurality of modules 106 may also be used as, signal processor(s), node machine(s), logic circuitries, and/or any other device or component that manipulates signals based on operational instructions. Further, the plurality of modules 106 can be used by hardware, by computer-readable instructions executed by the one or more hardware processors 102, or by a combination thereof. The plurality of modules 106 can include various sub-modules (not shown). The plurality of modules 106 may include computer-readable instructions that supplement applications or functions performed by the system 100 for the spike data optimization.

The data repository (or repository) 110 may include a plurality of abstracted piece of code for refinement and data that is processed, received, or generated as a result of the execution of the plurality of modules in the module(s) 106.

Although the data repository 110 is shown internal to the system 100, it will be noted that, in alternate embodiments, the data repository 110 can also be implemented external to the system 100, where the data repository 110 may be stored within a database (repository 110) communicatively coupled to the system 100. The data contained within such external database may be periodically updated. For example, new data may be added into the database (not shown in FIG. 1) and/or existing data may be modified and/or non-useful data may be deleted from the database. In one example, the data may be stored in an external system, such as a Lightweight Directory Access Protocol (LDAP) directory and a Relational Database Management System (RDBMS). Functions of the components of the system 100 are now explained with reference to steps in flow diagrams in FIG. 2 and FIG. 3.

Figure 2A:
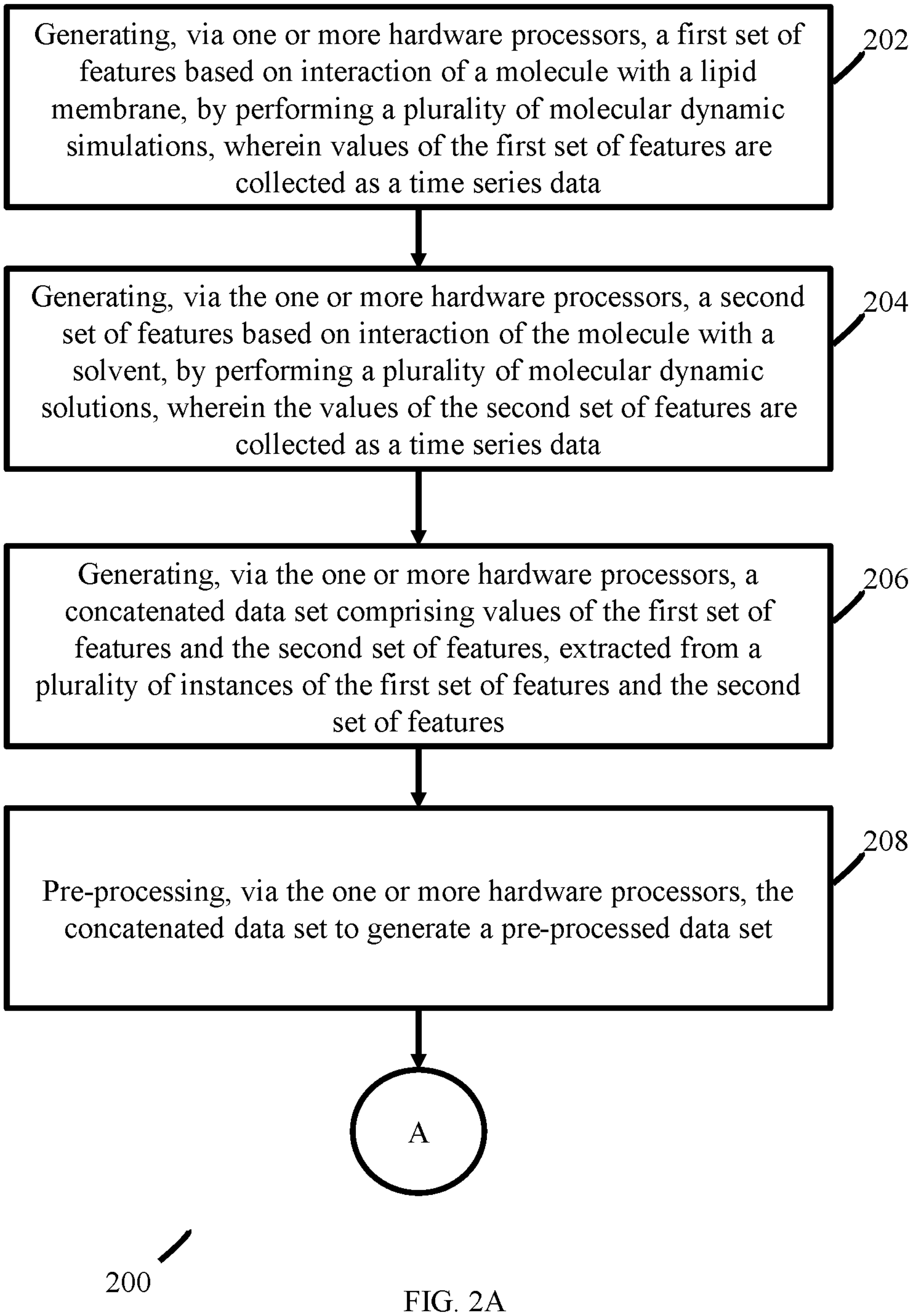
FIGS. 2A and 2B (collectively referred to as FIG. 2) is a flow diagram depicting steps involved in the process of generating the free energy of permeation, using the system of FIG. 1, according to some embodiments of the present disclosure.
Figure 2B:
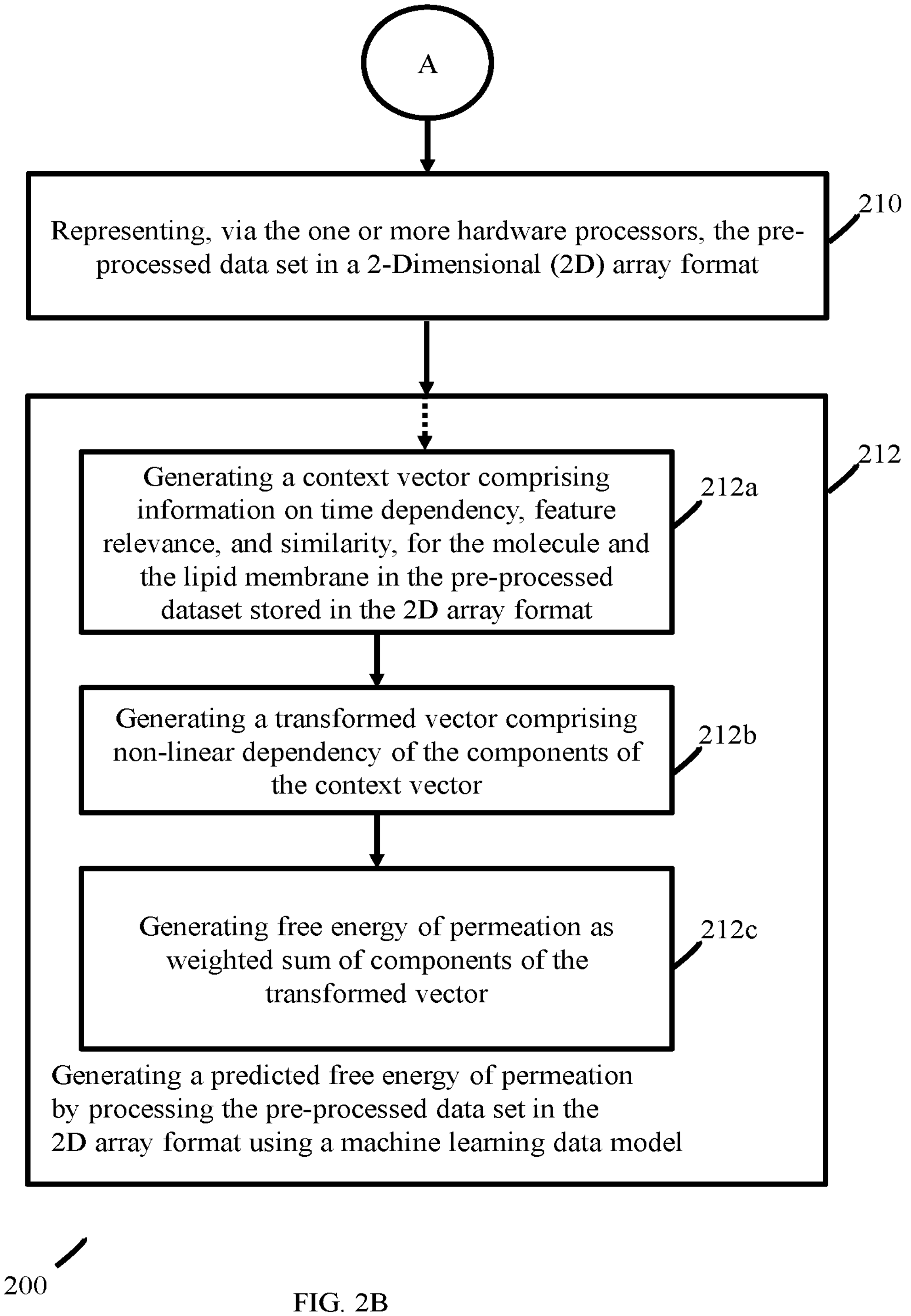

FIGS. 2A and 2B (collectively referred to as FIG. 2) is a flow diagram depicting steps involved in the process of determining the free energy of permeation, using the system of FIG. 1, according to some embodiments of the present disclosure.

At step 202 of a method 200 in FIG. 2, the one or more hardware processors 102 of the system 100 are configured to generate a first set of features based on interaction of a molecule with a lipid membrane, by performing a plurality of molecular dynamic simulations, wherein values of the first set of features are collected as a time series data. The first set of features comprises a) interaction energy (Lennard-Jones (LJ)) of the molecule with the lipid membrane, b) area per lipid of the lipid membrane, c) root mean square (RMS) deviation of a plurality of lipid molecules from a corresponding initial position, and d) RMS deviation for combination of a plurality of lipid membrane and the molecule.

Similarly, at step 204 of the method 200, the one or more hardware processors 102 of the system 100 are configured to generate a second set of features based on interaction of a molecule with a solvent, by performing the plurality of molecular dynamic simulations, wherein values of the second set of features are collected as a time series data. The second set of features comprises a) surface area of the molecule that can be accessed by the solvent, b) molecule-solvent enthalpy, c) LJ interaction energy between the molecule and the solvent, and d) bond energy of the molecule.

The steps 202 and 204 are further explained with reference to FIG. 3. In order to observe the interaction of one molecule with the solvent, at step 302 of method 300 in FIG. 3, the molecule in solvent system is generated by creating a simulation box and inserting the molecule and solvent molecules in the simulation box, wherein insertion refers to specifying the initial positions and velocities of all atoms in the system. For example, the molecule can be inserted at the center of the simulation box and the remaining box volume is filled up with an appropriate number of solvent molecules. In a similar manner, the molecule in lipid membrane system also is generated at step 304, by creating a simulation box and specifying initial positions and velocities of all atoms of the molecule and lipid molecules. For example, lipid molecules can be arranged in the form of a membrane of at least one type of lipid and the molecule can be inserted at the membrane midplane. Examples of molecule in lipid membrane system (bi-layer) and molecule in solvent system, are depicted in FIG. 4A and FIG. 4B respectively.

In an embodiment, selection of the solvent may be based on requirements. For example, the solvent may be water, or ethanol, or a combination thereof, in various concentration ratio. Similarly, the lipid membrane may be appropriately selected based on requirements. Examples of the membranes are, but not limited to skin's stratum corneum, intestine, and cell membrane.

After creating the molecule in solvent system and the molecule in lipid membrane system, the simulation conditions are specified. For example, the simulations can be performed at room temperature (300 K) or physiological temperature (310 K), and atmospheric pressure, for pharmaceutical applications. The initial molecule in solvent system and molecule in lipid membrane system are subjected to potential energy minimization, wherein any overlaps between one or more pairs of atoms are removed.

At each instance, value of each of the features forming the first set of features and the second set of features is obtained/calculated by the system 100. Further, at step 306, the system 100 generates a trajectory comprising position and velocities of atoms in the molecule in solvent system and the molecule in lipid membrane system, at all timesteps during the course of the plurality of molecular dynamic simulations. The molecular dynamics simulations are performed for the molecule in solvent system and the molecule in lipid system to obtain the trajectory, wherein the trajectory refer to or includes the positions and velocities of all the atoms at all time steps during the course of the plurality of molecular dynamic simulation. The plurality of features forming the first set of features and the plurality of features forming the second set of features are calculated/extracted from these trajectories at step 308 of the method 300. In the trajectory, each single configuration is referred to as a snapshot, which consists of the positions and velocities of all particles at a particular time instant. Values of each of the features forming the first set and the second set of features is calculated as a function of the positions and velocities of the particles. Thus, from the trajectory, multiple snapshots can be extracted, and accordingly the values of the features may be calculated.

Each of the features forming the first set of features and the second set of features is defined below:

1. Bondener (calculated from molecule-solvent simulation):

For each bond in the molecule, there is a corresponding bond energy. This value depends on (or is a complex mathematical function of) an instantaneous bond length during a simulation, equilibrium bond length, and bond constant. The equilibrium bond length, and bond constant are specified as a part of the interatomic interactions while creating molecular models. As the coordinates of all molecules are known, the distance between two bonded particles is calculated as the instantaneous bond length. The bond energies of all individual bonds of the drug molecules are added and the sum is divided by the total number of bonds to compute the bondener feature.

2. Lj-mol-wat (calculated from molecule-solvent simulation):

Lennard-Jones (LJ) interactions are non-bonded interactions between two particles. It depends on the nature of the individual particles (there are two parameters a and c that defines the particles) and their interparticle distance. The LJ interaction between the molecule and molecules of the solvent is calculated because the coordinates are known for each instance. All the individual interaction values are added, and the sum is divided by the number of molecules.

3. Molwat-enthalpy (calculated from molecule-solvent simulation):

Complex mathematical function of the coordinates of all particles in the molecule-solvent simulation.

4. Sasa (calculated from molecule-solvent simulation):

Surface area of the molecule that can be accessed by the solvent. It is also a complex mathematical function of coordinates.

5. Lj-mol-lip (calculated from molecule-lipid membrane simulation):

Similar to lj-mol-wat, but interactions are calculated between the molecule and lipid membrane.

6. Apl (calculated from molecule-lipid membrane simulation):

Apl is area per lipid. The lipids membrane exists in the form of bilayers consisting of two leaflets (top and bottom). The Apl is calculated as the cross-sectional area of the simulation box divided by the number of lipids in each leaflet.

7. Rmsd-lip (calculated from molecule-lipid membrane simulation):

Root mean square deviation of the lipid particles from initial position. It can be calculated from the coordinates of a plurality of lipid membrane particles at an instance.

8. Rmsd-mollip (calculated from molecule-lipid membrane simulation):

Similar to rmsd-lip, but combination of lipid membrane and molecules is considered.

Figure 3:
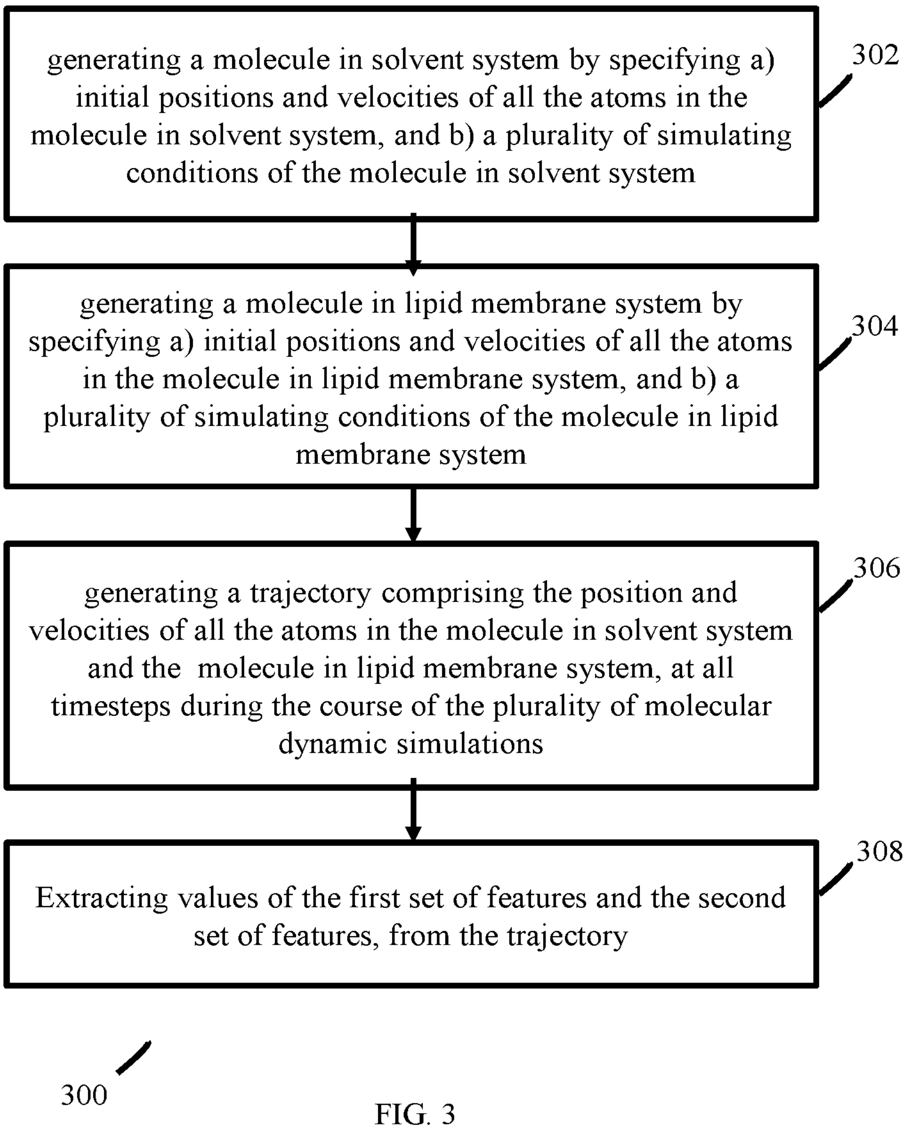
FIG. 3 is a flow diagram depicting steps involved in the process of extracting values of a first set of features and a second set of features, using the system of FIG. 1, in accordance with some embodiments of the present disclosure.
Figure 4A:
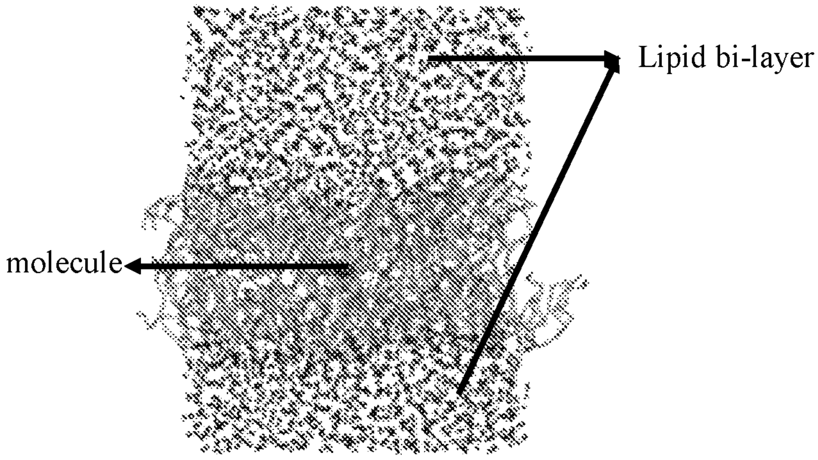
FIGS. 4A and 4B depict examples of molecule in lipid membrane system (bi-layer) and molecule in solvent system, in accordance with some embodiments of the present disclosure.
Figure 4B:
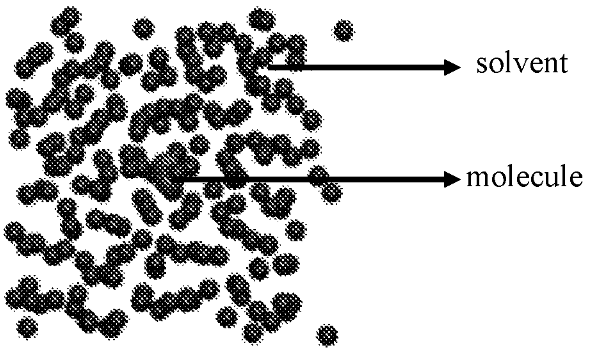

After generating the first set of features and the second set of features using the method 300 of FIG. 3, further at step 206 of the method 200, the system 100 generates, via the one or more hardware processors, a concatenated data set comprising values of the first set of features and the second set of features, extracted from a plurality of instances of the first set of features and the second set of features. Further, at step 208 of the method 200, the system 100 pre-processes, via the one or more hardware processors, the concatenated data set to generate a pre-processed data set. Pre-processing the dataset comprises steps such as but not limited to data scaling. The system 100 may use any suitable technique for the data scaling. In another embodiment, in addition to data scaling, the system 100 may perform any other required actions so as to condition the data in the concatenated data set as required for further processing. For example, the system 100 may change formatting of the data to match a required format, as part of the pre-processing.

Further, at step 210 of the method 200, the system 100 represents, via the one or more hardware processors, the pre-processed data set in a 2-Dimensional (2D) array format. The 2D array format allows representing the time-series data with multiple features. As compared to one-dimensional (1D) static/average features, the 2D array format allows feeding comparatively larger amount of data.

Further, at step 212 of the method 200, the system 100 generates a free energy of permeation by processing the pre-processed data set in the 2D array format using a machine learning data model. The machine learning data model is generated by using data obtained for a plurality of molecule-lipid layer combinations i.e. different molecules and different lipid layers, so that the machine learning data model can be used for determining free energy of permeation for different molecule-lipid layer combinations received as input. Processing the pre-processed data set in the 2D array format using a machine learning data model includes the following sub-steps.

At sub-step 212A, the system 100 generates a context vector comprising information on time dependency, feature relevance, and similarity, for a plurality of molecules in the pre-processed dataset stored in the 2D array format. The 2D array (alternately referred to as 'array') also represents the evolution of the molecule in solvent system and/or the molecule in lipid membrane system with time. Consider that the first row of the array represents the features of the molecule in solvent system and/or the molecule in lipid membrane system at a particular time instant, the second row represents the features of the molecule in solvent system and/or the molecule in lipid membrane system at a later time instant, and so on (as given in Table. 1). Hence, by moving across the rows, information on how the features of the molecule in solvent system and/or the molecule in lipid membrane system changes with time is obtained. This is referred to as the time dependency. Similarly, as change in values of features across different time instances is a crucial data, it is important that the values of same features are monitored and calculated across instances, and is referred to as the feature dependency. The feature relevance means that various model weights used while building the data model are adjusted during a training process in such a way that the output is sensitive to some features more than others. Higher relevance of a feature indicates a stronger correlation between a feature and the output. The training process of any machine learning model involves tuning the weights and biases using an optimization approach, so that the output accuracy is maximized. The data model learns the relative importance of each feature during training. The context vector is calculated using an attention layer of the data model, and captures similarity between different molecules. For example, the context vectors of two hydrophobic molecules (negative free energy of permeation) are closer to each other in comparison context vectors of molecules having hydrophobic and a hydrophilic nature. The context vector also represents a relative importance of the features for computing the free energy of permeation. The context vector also reduces a sequential information into a simple vector that can be mapped to output of the data model i.e. the free energy of permeation.

At sub-step 212*b*, the system 100 generates a transformed vector comprising information on non-linear dependency of the components of the context vector. Further, at sub-step 212*c*, the system 100 determines the free energy of permeation as weighted sum of components of the transformed vector.

The free energy of permeation may be then provided as a recommendation to the user, by the system 100. In an embodiment, the free energy of permeation may be displayed to the user using an appropriate display interface of the system 100 or any other user device (for example, a mobile phone, a tablet PC and so on) that is configured to communicate with the system 100.

Experimental Data:

Values of the features forming the first feature set and the second feature set were obtained by conducting the molecular dynamics simulations, for a selected drug-lipid membrane combination, are represented by a 2D array of time series features, such that there are 8 columns (no. of features) and 350 rows (no. of time steps) for every sample, as given below:

TABLE 1

| | Feat 1 | Feat 2 | Feat 3 | Feat 4 | Feat 5 | Feat 6 | Feat 7 | Feat 8 |
|---|---|---|---|---|---|---|---|---|
| Step 1 | 2.960 | −37.671 | −4874.3 | 0.801 | −39.273 | 0.587 | 1.908 | 1.907 |
| Step 2 | 17.12 | −42.761 | −4944.4 | 0.704 | −37.091 | 0.599 | 1.833 | 1.831 |
| . | . | . | . | . | . | . | . | . |
| . | . | . | . | . | . | . | . | . |
| . | . | . | . | . | . | . | . | . |
| Step 350 | 2.441 | −39.602 | −4925.7 | 0.818 | −34.785 | 0.589 | 3.316 | 3.313 |

Where,

Feat 1 (Feature 1) is Bondener: contributes to the energetics

Feat 2 (Feature 2) is Lj-mol-wat—contributes to the energetics

Feat 3 (Feature 3) is Molwat-enthalpy—contributes to the energetics

Feat 4 (Feature 4) is Sasa—related to hydrophobic effect

Feat 5 (Feature 5) is Lj-mol-lip—contributes to the energetics

Feat 6 (Feature 6) is Apl—determines how much space the lipid bilayer allows to facilitate the entry of drug; indirectly related to entropy Feat 7 (Feature 7) is Rmsd-lip—related to entropy, determines if the lipid molecules are mobile enough to readjust their configuration Feat 8 (Feature 8) is Rmsd-mollip—related to entropy, determines the combined mobility of lipids and drug The data, which is a raw input, is scaled using a Min-Max scaler, and the scaled input matrix is fed to the data model. The scaled input of the above sample is given as follows (in Table. 2):

TABLE 2

| | Feat 1 | Feat 2 | Feat 3 | Feat 4 | Feat 5 | Feat 6 | Feat 7 | Feat 8 |
|---|---|---|---|---|---|---|---|---|
| Step 1 | 0.0945 | 0.5097 | 0.4793 | 0.4717 | 0.3315 | 0.0899 | 0.3273 | 0.3267 |
| Step 2 | 0.5469 | 0.4385 | 0.3763 | 0.2915 | 0.3670 | 0.1209 | 0.3074 | 0.3068 |
| . | . | . | . | . | . | . | . | . |
| . | . | . | . | . | . | . | . | . |
| . | . | . | . | . | . | . | . | . |
| Step 350 | 0.0780 | 0.4827 | 0.4037 | 0.5042 | 0.4045 | 0.0962 | 0.6994 | 0.6980 |

Figure 5:
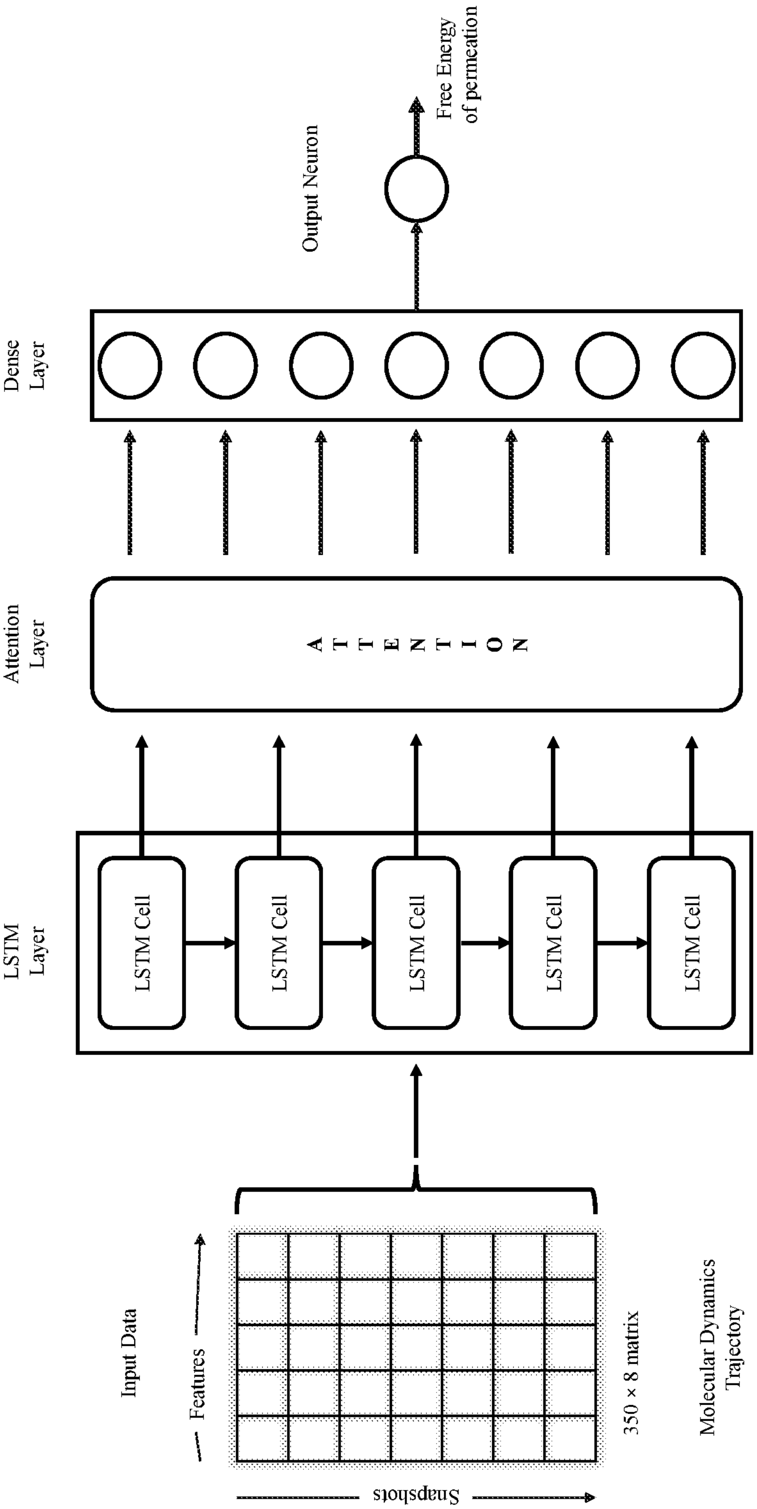
FIG. 5 is an example of a neural network architecture used for determining the free energy of permeation by the system of FIG. 1, in accordance with some embodiments of the present disclosure.
Figure 6:
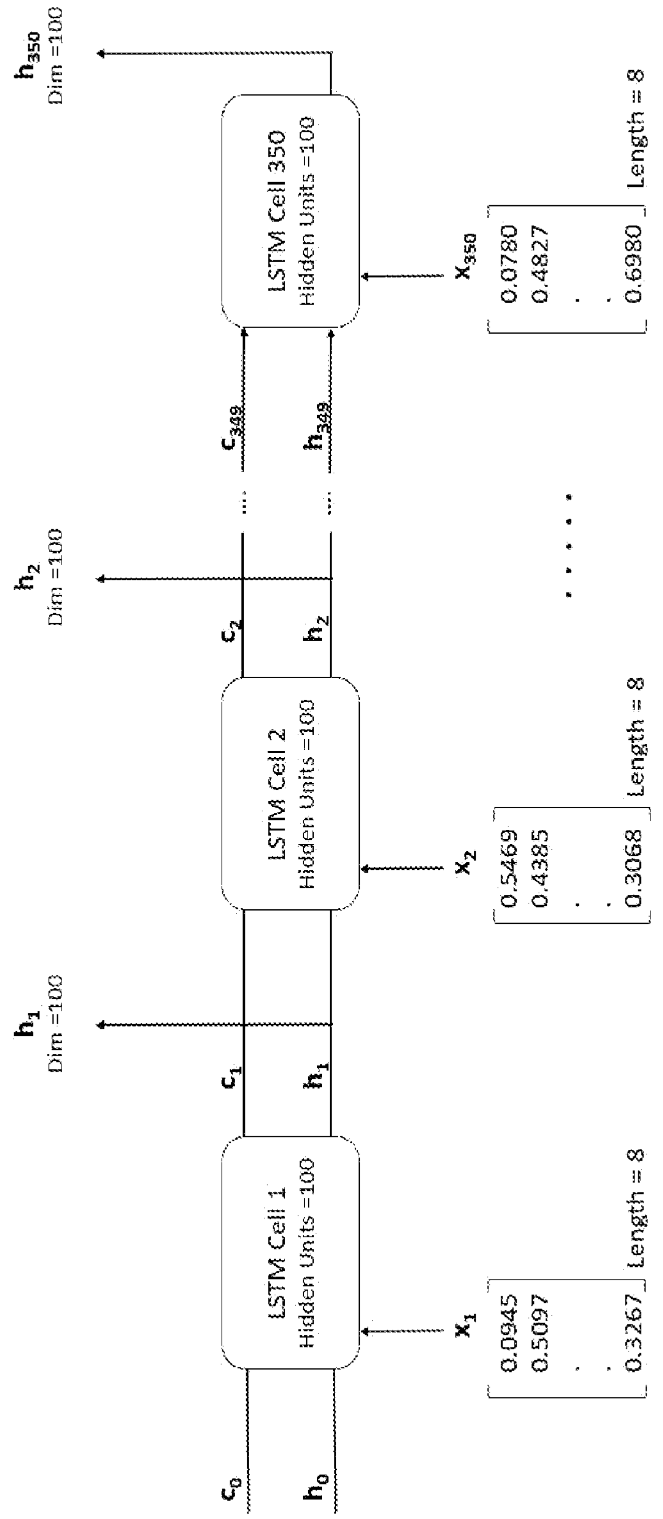
FIG. 6 is an example architecture of LSTM layer of the neural network of FIG. 5, in accordance with some embodiments of the present disclosure.

This data is further used to train the data model comprising the LSTM layers and the attention layer of a neural network. Example architecture of the neural network is depicted in FIG. 5. Further, example architecture of the LSTM layer of the neural network of FIG. 5 is depicted in FIG. 6. As depicted in FIG. 6, the LSTM layer encodes the physically-relevant features into computational states for further processing. The LSTM layer uses feature vectors ($x_1$, $x_2$, . . . , $x_{350}$) of length 8 corresponding to Step 1, Step 2, . . . , Step 350. Each LSTM cell of the LSTM layer takes the feature vector at each time step ($x_t$), hidden state of the previous cell ($h_{t-1}$), and the previous cell state ($c_{t-1}$) as input, and produces the cell state ($c_t$) and hidden state ($h_t$) as output. The hidden states $h_1$, $h_2$, . . . , $h_{350}$ are of length 100 (corresponding to 100 hidden units), and they are obtained by a series of mathematical transformations of the inputs data. From the LSTM layer, an output of 350 hidden states of length 100 were obtained as output which is then fed as input to the attention layer.

Layer weights that determine the hidden states were optimized during training of the data model (i.e. training phase) such that the time dependency of the features is preserved. As free energy depends on the distribution of possible states of the molecule in solvent system and/or the molecule in lipid membrane system, how states evolve with time and identify the relevant states attained during a process is to be considered, both of which are accomplished by the LSTM layer. Thus, the LSTM layer is a way of encoding the input so that subsequent layers can learn relevant information from the hidden states.

Figure 7:
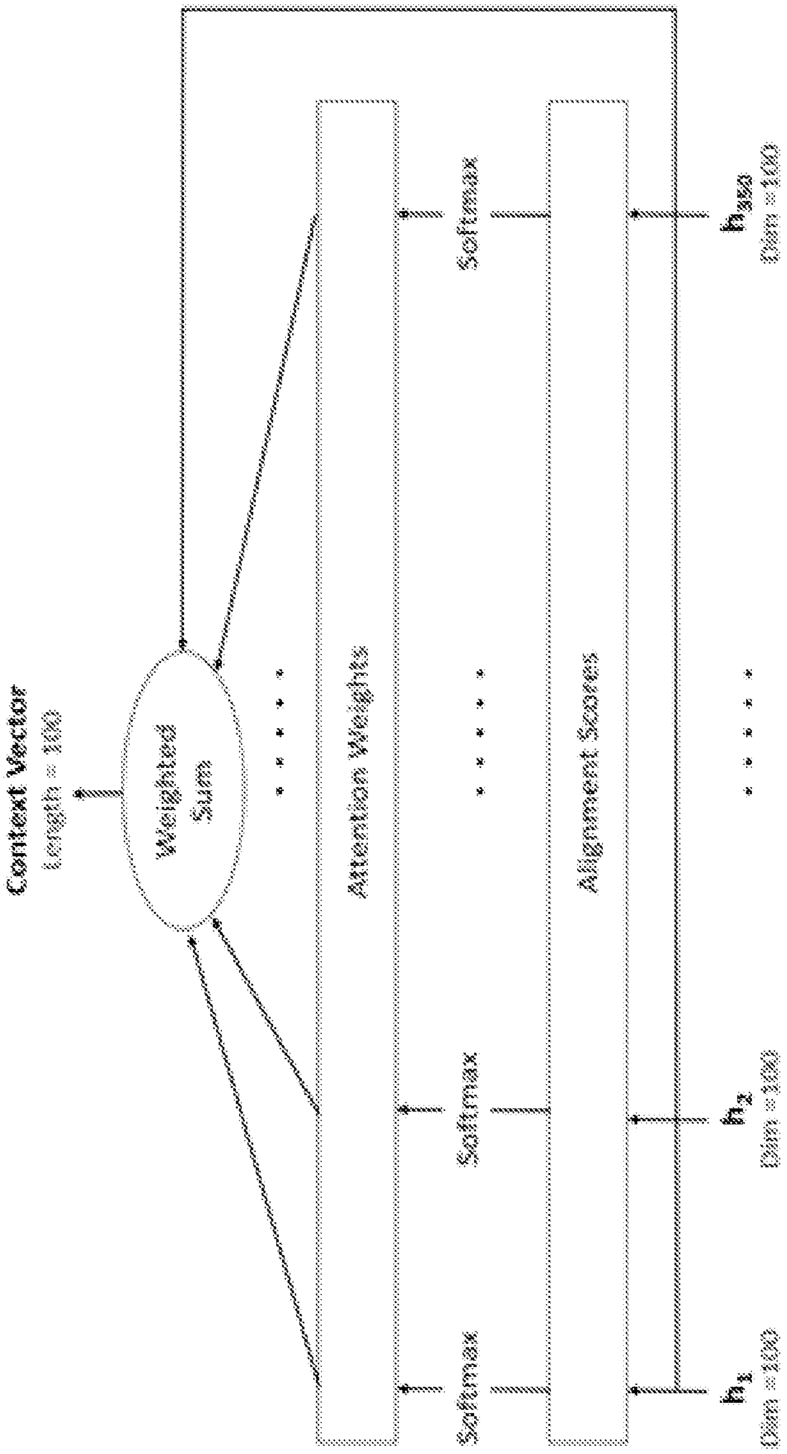
FIG. 7 is an example architecture of an attention layer of the neural network of FIG. 5, in accordance with some embodiments of the present disclosure.

The hidden states from the LSTM layer are fed into the Attention layer to generate the context vector. An example architecture of the attention layer of the neural network of FIG. 5 is depicted in FIG. 7. The context vector captures similarity between different molecules. For example, the context vectors of two hydrophobic molecules (negative free energy of permeation) are closer to each other in comparison context vectors of molecules having hydrophobic and a hydrophilic nature. The context vector also represents a relative importance of the features for computing the free energy of permeation. The context vector also reduces a sequential information into a simple vector that can be mapped to output of the data model i.e. the free energy of permeation.

From the encoded hidden states of the previous LSTM layers, a plurality of alignment scores were calculated using a single-layered feedforward network by the attention layer. Then, the attention weights were computed by applying a SoftMax activation function on the alignment scores. Finally, a weighted sum over all input time steps is performed to generate the context vector. The relevant equations are as follows:

$$a = \tanh(W^a h + b^a) \rightarrow \quad (1)$$

where 'a' is the alignment score matrix, h is the matrix of hidden states from the LSTM layer, $W^a$ and $b^a$ are the weights and biases of the feedforward network, and 'tanh' is the activation function.

$$\alpha = \mathrm{SoftMax}(a) \rightarrow \quad (2)$$

where a is the attention weight matrix.

$$C^o = \sum \alpha \cdot h \rightarrow \quad (3)$$

where $C^o$ is the context vector of length 100, calculated as the weighted sum from the hidden states. The LSTM layer and the attention layer were sequentially used to learn the time dependency, the feature relevance, and the similarity between molecules.

Further, a dense layer and an output neuron mapped the context vector to the free energy of permeation through a series of mathematical transformations. The context vector encoded all the relevant information required for estimating the free energy of permeation, and the dense layer learns the non-linear dependence of the elements of the context vector with the free energy. Hence, by passing the context vector through the dense layer, another vector of same length that incorporates the nonlinearity, was obtained, and is represented as:

$$D = ReLU(W^d \cdot C^o + b^d) \rightarrow \quad (4)$$

where, $W^d$ and $b^d$ are the weight and bias matrices of the dense layer, $C^o$ is the context vector from the attention layer, D is the output of the dense layer, and ReLU is the activation function. Similar to the context vector, the output of the dense layer was also of length 100.

Then the free energy of permeation was estimated in the output neuron as the weighted sum of the elements of the transformed vector of the dense layer.

$$\text{Free Energy of Permeation} = w_1 \cdot D_1 + w_2 \cdot D_2 + \ldots + w_{100} \cdot D_{100} + b_{output} \rightarrow \quad (5)$$

where, $D_1, D_2, \ldots, D_{100}$ are the elements of the vector D (output of the dense layer); $w_1, w_2, \ldots, w_{100}$ are the weights of the output neuron, and $b_{output}$ is the bias.

While estimating the free energy of permeation, a Mean Absolute Error (MAE) loss function was used to train the data model, which is a standard practice for regression problems. During the training phase, the deviations of the free energy values calculated by the model from the actual values were backpropagated, and the weights of all the layers were adjusted such that this deviation is minimized. After the training phase, the trained data model then used for processing real-time inputs and for generating value of the free energy of permeation corresponding to values of the real-time inputs.

Results:

For the experiments, the drug-lipid membrane combinations in the training, validation, and test datasets were 510, 57, and 63. The machine learning model was additionally validated on an out-of-distribution dataset of 50 drug-lipid combinations. The determined values of free energy of permeation (alternately referred to as 'prediction' or 'free energy estimation' while explaining the experimental results) were compared against actual free energy values computed using state of the art approaches. For the data model to be reliable for high-throughput free energy estimation, statistical error must be within tolerable limits. Due to the natural thermal fluctuations in MD simulation-based methods, an error around 1-2 $k_BT$ (~0.6-1.2 kcal/mol at 300 K) can be considered extremely accurate. The model was trained for 1000 epochs to reduce the validation loss, and the MAE and the coefficient of determination ($R^2$) was reported to evaluate model performance.

Table 3: Mean Absolute Error (MAE) (in kcal/mol), and Coefficient of Determination ($R^2$) of the deep learning model on the training, validation, test, and out-of-distribution sets:

| Training Set | | Validation Set | | Test Set | | Out-of-dist Set | |
|---|---|---|---|---|---|---|---|
| MAE | $R^2$ | MAE | $R^2$ | MAE | $R^2$ | MAE | $R^2$ |
| 0.24 | 0.996 | 0.34 | 0.992 | 0.46 | 0.984 | 1.50 | 0.82 |

Figure 8A:
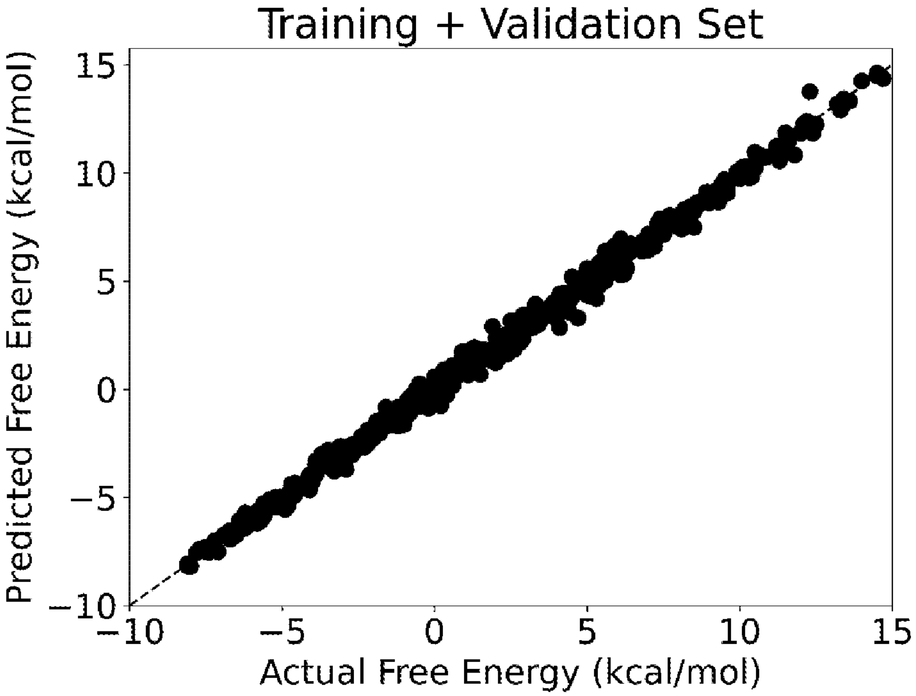
FIGS. 8A, 8B, and 8C (collectively referred to as FIG. 8) depict plots of values of free energy of permeation obtained for different datasets, in an experimental setup of the system of FIG. 1, in accordance with some embodiments of the present disclosure.
Figure 8B:
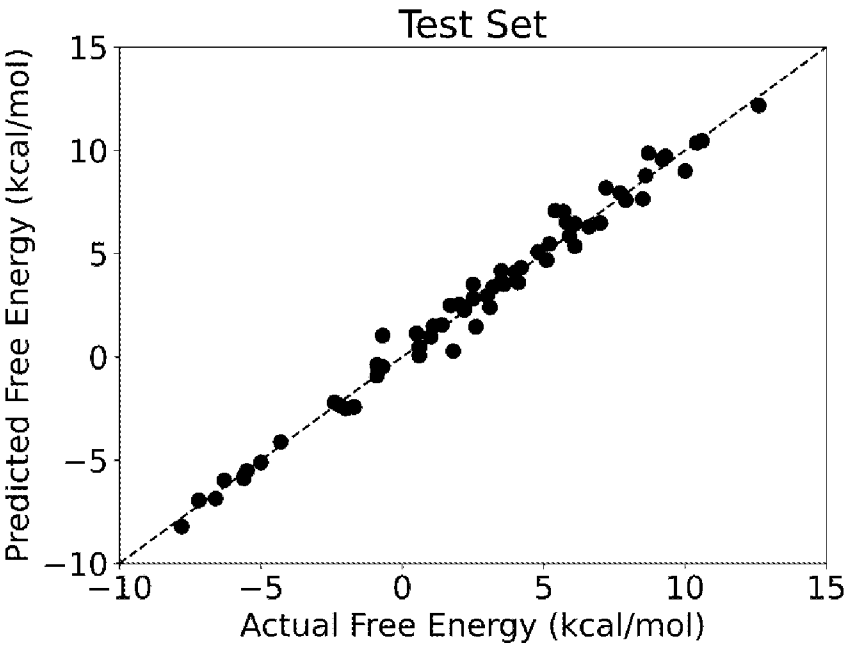
Figure 8C:
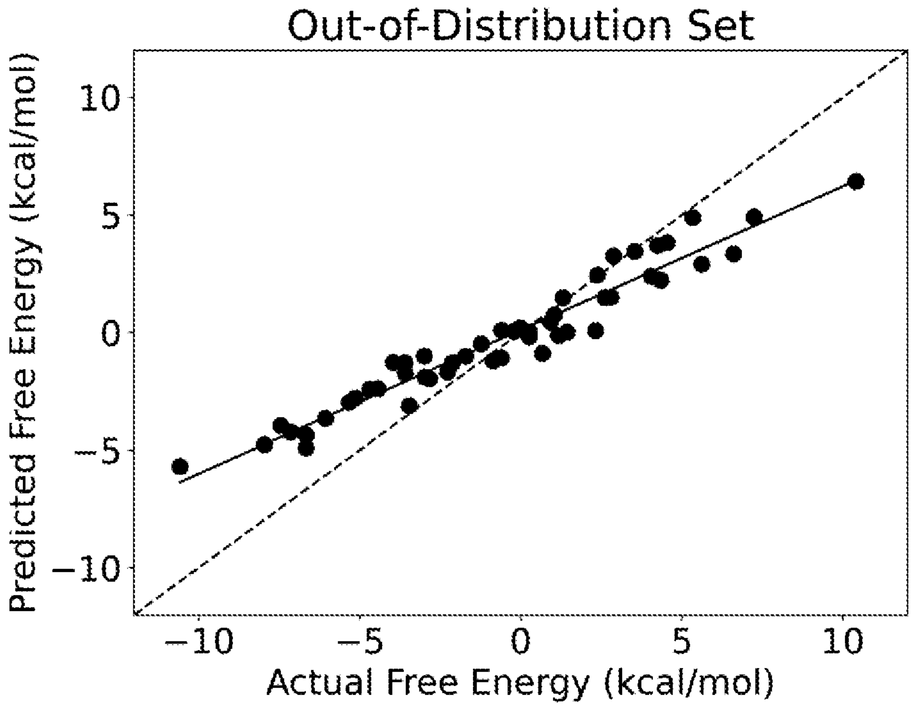

Table 3 summarizes the performance metrics of the model on the training, validation, test, and out-of-distribution sets. The results show that the model is powerful in predicting the free energy of permeation from the multidimensional time series generated using MD simulations. The MAEs on the training, validation, and test datasets are within acceptable limits and lower than state-of-the-art data-driven methods, with $R^2$ being around 0.99. The comparable results in all three cases indicate the generalizability of the data model being used by system 100. The prediction accuracy for the out-of-distribution dataset is lower than the test set due to the difference in drug chemistry, but it still outperforms state-of-the-art data-driven methods. FIGS. 8A, 8B, and 8C plot the determined free energies with the actual free energies from the dataset.

It is vital in virtual screening applications to correctly rank molecules based on their relative free energy of permeation even if the absolute predictions are not too accurate. Generally, a few top candidates are chosen from hundreds or thousands after screening and subjected to experiments. The Pearson correlation coefficient, which measures the linear correlation between two variables, and Spearman's rank correlation coefficient, which measures the extent of monotonicity between two variables, for the model were calculated to be 0.969 and 0.967, respectively, on the out-of-distribution set. Hence, the data model can be reliably deployed to screen small drug-like molecules. The system was designed to devise a solution to estimate the free energy of permeation of small molecules across membranes with similar accuracy as MD simulation-based methods but at a much faster rate. As most virtual screening tasks involve hundreds or thousands of molecules, the computational paradigm must be well equipped to handle them within a realistic time frame. The system and method in the embodiments disclosed herein were benchmarked on a single AMD Ryzen 5 3500U processor with 4 GB RAM. The drug-water simulation of each system, including equilibration, took around 6.5 minutes, whereas 105 minutes were required for drug-lipid membrane simulations. The approximate time required for estimating free energy of permeation for each drug-lipid combination on the same computer using state-of-the-art purely molecular simulation techniques was found to be to 55 hours. Comparing results of the model of the system 100 with a state of the art system, it was observed that a speed-up of about 25× can be achieved by following our system and method. Similar speed-ups are expected for other system architectures like GPUs and clusters.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem of determining free energy of permeation. The embodiment, thus provides a method and system for determining a free energy of permeation for molecules. Moreover, the embodiments herein further provides a mechanism to use features generated based on interaction of molecules with solvents and lipid membrane together to determine the free energy of permeation.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:

generating, via one or more hardware processors, a first set of features based on interaction of a molecule with a lipid membrane, by performing a plurality of molecular dynamics simulations, wherein values of the first set of features are collected as a time series data;

generating, via the one or more hardware processors, a second set of features based on interaction of the molecule with a solvent by performing the plurality of molecular dynamics simulations, wherein values of the second set of features are collected as a time series data;

generating, via the one or more hardware processors, a concatenated data set comprising values of the first set of features and the second set of features, extracted from a plurality of instances of the time series data of the first set of features and the second set of features;

pre-processing, via the one or more hardware processors, the concatenated data set to generate a pre-processed data set;

representing, via the one or more hardware processors, the pre-processed data set in a 2-Dimensional (2D) array format; and generating, via the one or more hardware processors, a free energy of permeation by processing the pre-processed data set in the 2D array format using a machine learning data model, comprising:

generating a context vector comprising information on a time dependency, a feature relevance, and a similarity, for the molecule and the lipid membrane in the pre-processed data set stored in the 2D array format;

generating a transformed vector comprising information on non-linear dependency of the components of the context vector; and generating the free energy of permeation as weighted sum of components of the transformed vector.

2. The method of claim 1, wherein the first set of features comprises a) interaction energy (Lennard-Jones (LJ)) of the molecule with the lipid membrane, b) area per lipid of the lipid membrane, c) root mean square (RMS) deviation of a plurality of lipid molecules from a corresponding initial position, and d) RMS deviation for combination of a plurality of lipid membrane and the molecule.

3. The method of claim 1, wherein the second set of features comprises a) surface area of the molecule that can be accessed by the solvent, b) molecule-solvent enthalpy, c) LJ interaction energy between the molecule and the solvent, and d) bond energy of the molecule.

4. The method of claim 1, wherein generating the first set of features and the second set of features comprises:

generating a molecule in solvent system by specifying a) initial positions and velocities of all the atoms in the molecule in solvent system, and b) a plurality of simulating conditions of the molecule in solvent system;

generating a molecule in lipid membrane system by specifying a) initial positions and velocities of all the atoms in the molecule in lipid membrane system, and b) a plurality of simulating conditions of the molecule in lipid membrane system;

generating a trajectory comprising the position and velocities of all the atoms in the molecule in solvent system and the molecule in lipid membrane system, at all timesteps during the course of the plurality of molecular dynamic simulations; and extracting values of the first set of features and the second set of features, from the trajectory.

5. A system, comprising:

one or more hardware processors;

a communication interface; and a memory storing a plurality of instructions, wherein the plurality of instructions when executed, cause the one or more hardware processors to:

generate a first set of features based on interaction of a molecule with a lipid membrane, by performing a plurality of molecular dynamics simulations, wherein values of the first set of features are collected as a time series data;

generate a second set of features based on interaction of the molecule with a solvent by performing the plurality of molecular dynamics simulations, wherein values of the second set of features are collected as a time series data;

generate a concatenated data set comprising values of the first set of features and the second set of features, extracted from a plurality of instances of the time series data of the first set of features and the second set of features;

pre-process the concatenated data set to generate a pre-processed data set;

represent the pre-processed data set in a 2-Dimensional (2D) array format; and generate a free energy of permeation by processing the pre-processed data set in the 2D array format using a machine learning data model, by:

generating a context vector comprising information on time dependency, feature relevance, and similarity, for the molecule and the lipid membrane in the pre-processed data set stored in the 2D array format;

generating a transformed vector comprising information on non-linear dependency of the components of the context vector; and generating the free energy of permeation as weighted sum of components of the transformed vector.

6. The system of claim 5, wherein the first set of features comprises a) interaction energy (Lennard-Jones (LJ)) of the molecule with the lipid membrane, b) area per lipid of the lipid membrane, c) RMS deviation of a plurality of lipid molecules from a corresponding initial position, and d) RMS deviation for combination of a plurality of lipid membrane and the molecule.

7. The system of claim 5, wherein the second set of features comprises a) surface area of the molecule that can be accessed by the solvent, b) molecule-solvent enthalpy, c) LJ interaction energy of drug molecule in the solvent, and d) bond energy of the molecule.

8. The system of claim 5, wherein the one or more hardware processors are configured to generate the first set of features and the second set of features by:

generating a molecule in solvent system by specifying a) initial positions and velocities of all the atoms in the molecule in solvent system, and b) a plurality of simulating conditions of the molecule in solvent system;

generating a molecule in lipid membrane system by specifying a) initial positions and velocities of all the atoms in the molecule in lipid membrane system, and b) a plurality of simulating conditions of the molecule in lipid membrane system;

generating a trajectory comprising the position and velocities of all the atoms in the molecule in solvent system and the molecule in lipid membrane system, at all timesteps during the course of the plurality of molecular dynamic simulations; and extracting values of the first set of features and the second set of features, from the trajectory.

9. One or more non-transitory machine-readable information storage mediums comprising one or more instructions which when executed by one or more hardware processors cause:

generating a first set of features based on interaction of a molecule with a lipid membrane, by performing a plurality of molecular dynamics simulations, wherein values of the first set of features are collected as a time series data;

generating a second set of features based on interaction of the molecule with a solvent by performing the plurality of molecular dynamics simulations, wherein values of the second set of features are collected as a time series data;

generating a concatenated data set comprising values of the first set of features and the second set of features, extracted from a plurality of instances of the time series data of the first set of features and the second set of features;

pre-processing, the concatenated data set to generate a pre-processed data set;

representing, the pre-processed data set in a 2-Dimensional (2D) array format; and generating, a free energy of permeation by processing the pre-processed data set in the 2D array format using a machine learning data model, comprising:

generating a context vector comprising information on a time dependency, a feature relevance, and a similarity, for the molecule and the lipid membrane in the pre-processed data set stored in the 2D array format;

generating a transformed vector comprising information on non-linear dependency of the components of the context vector; and generating the free energy of permeation as weighted sum of components of the transformed vector.

10. The one or more non-transitory machine-readable information storage mediums of claim 9, wherein the first set of features comprises a) interaction energy (Lennard-Jones (LJ)) of the molecule with the lipid membrane, b) area per lipid of the lipid membrane, c) root mean square (RMS) deviation of a plurality of lipid molecules from a corresponding initial position, and d) RMS deviation for combination of a plurality of lipid membrane and the molecule.

11. The one or more non-transitory machine-readable information storage mediums of claim 9, wherein the second set of features comprises a) surface area of the molecule that can be accessed by the solvent, b) molecule-solvent enthalpy, c) LJ interaction energy between the molecule and the solvent, and d) bond energy of the molecule.

12. The one or more non-transitory machine-readable information storage mediums of claim 9, wherein generating the first set of features and the second set of features comprises:

generating a molecule in solvent system by specifying a) initial positions and velocities of all the atoms in the molecule in solvent system, and b) a plurality of simulating conditions of the molecule in solvent system;

generating a molecule in lipid membrane system by specifying a) initial positions and velocities of all the atoms in the molecule in lipid membrane system, and b) a plurality of simulating conditions of the molecule in lipid membrane system;

generating a trajectory comprising the position and velocities of all the atoms in the molecule in solvent system and the molecule in lipid membrane system, at all timesteps during the course of the plurality of molecular dynamic simulations; and extracting values of the first set of features and the second set of features, from the trajectory.

* * * * *